United States Patent
Burke et al.

[11] Patent Number: 5,562,912
[45] Date of Patent: Oct. 8, 1996

[54] LIQUID SKIN CLEANSER COMPOSITION WITH REDUCED SKIN IRRITATION AND IMPROVED AFTER-FEEL

[75] Inventors: John J. Burke, Lake Mohawk, N.J.; Joanne P. Gorczyca, Livonia, Mich.

[73] Assignee: BASF Corporation, Mount Olive, N.J.

[21] Appl. No.: 537,335

[22] Filed: Dec. 6, 1995

Related U.S. Application Data

[63] Continuation-in-part of Ser. No. 258,164, Jul. 10, 1994, abandoned.

[51] Int. Cl.$^6$ ............................................. A61K 7/50
[52] U.S. Cl. ............... 424/401; 424/70.15; 424/70.19; 424/70.22; 424/70.31; 424/78.02; 514/844; 514/846; 510/138; 510/158
[58] Field of Search ............... 424/401, 78.02, 424/70.19, 70.15, 70.22, 70.31, 78.36; 514/844, 846; 252/DIG. 5, 174.21

[56] References Cited

U.S. PATENT DOCUMENTS

| | | | |
|---|---|---|---|
| 3,829,563 | 8/1974 | Barry et al. | 514/846 |
| 4,803,010 | 2/1989 | Ogino et al. | 252/174.21 |
| 5,030,374 | 7/1991 | Tranner | 514/846 |
| 5,037,484 | 8/1991 | Su et al. | 252/174.21 |
| 5,057,311 | 10/1991 | Kamegai et al. | 252/174.17 |
| 5,139,770 | 8/1992 | Shih et al. | 424/401 |
| 5,284,833 | 2/1994 | McAnalley et al. | 514/846 |
| 5,385,685 | 1/1995 | Humphreys et al. | 514/844 |

*Primary Examiner*—Amy Hulina
*Attorney, Agent, or Firm*—Joanne P. Will

[57] ABSTRACT

An improved liquid skin cleanser composition will have about 0.1–25% by weight of at least one EO/PO/EO triblock nonionic surfactant having the formula:

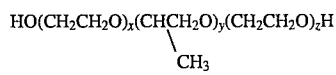

wherein neither x or z can be 0; the sum of x and z is within the range of about 62 to 535, the value of y is within the range of about 15 to 65. Also present will be about 0.1–25% by weight polyvinylpyrrolidone having the formula:

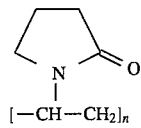

wherein the value of n ranges from about 100 to 30,000.

18 Claims, No Drawings

LIQUID SKIN CLEANSER COMPOSITION WITH REDUCED SKIN IRRITATION AND IMPROVED AFTER-FEEL

This is a continuation-in-part application of application U.S. Ser. No. 08/258,164, filed on Jul. 10, 1994, now abandoned.

FIELD OF THE INVENTION

The present invention relates to a liquid skin cleanser composition, and more specifically, to a liquid skin cleanser composition which improves skin-after-feel, reduces skin irritation, and increases tactile creaminess of the lather.

BACKGROUND OF THE INVENTION

The liquid skin cleanser market is growing at a rapid rate. These products became popular originally because of their convenience, reduced mess at the sink and implied improved hygiene compared to bar soaps. Most formulas were based on soap because it is inexpensive. There was later a move to add antibacterial ingredients to add value to the category and ultimately increase market share. Most recent attempts at value added features are to provide mildness and skin after-feel without sacrificing luxurious lather associated with soap-based formulas. The use of glycerin, sorbitol, vitamin E, coco fatty acid derivatives/salts, alkyl quaternary salts, sugar esters and the like are used to support foam stability and provide skin after-feel. Such additives are well known in the art. Many of these additives are either expensive, compromise lather quality or add tackiness during or after the drying stage after use. Unfortunately also, the soap-based formula has not been upgraded along with the additive features, presumably because of the added cost associated with the skin care additives.

U.S. Pat. No. 5,057,311, issued to the Kao Corporation, relates to the combination of an alkyl saccharide type surfactant and a cationic polymer to impart mildness and after feel to skin and hair. It is well known in the art that cationic materials have an affinity to skin and that saccharides (sugars) impart mildness. Kao has synthesized chemical structures that possess the required chemical moieties to achieve the intended results. On the other hand, the patentees do not teach or anticipate the use of ethylene oxide—propylene oxide—ethylene oxide (EO/PO/EO) tri-block copolymer surfactants in combination with polyvinylpyrrolidone (PVP). In fact, such tri-block copolymer surfactants are notorious for their low foam character and are used in other applications for just this reason. Nonionic EO/PO/EO tri-block copolymers make excellent additives for pesticide formulations, automatic dishwashing detergents, and floor cleaners, etc. It is therefore unexpected for these copolymer surfactants to find utility in liquid skin cleansers, for which the consumer demands rich, luxurious lather.

It has now been found that the combination of nonionic EO/PO/EO tri-block copolymers together with the polyvinylpyrrolidone improves not only the foam character of liquid skin cleansers, but also the hand feel and mildness characteristics as well.

OBJECTS OF THE INVENTION

It is therefore an object of the present invention to provide an improved liquid skin cleanser composition.

It is a further object of the invention to provide an improved liquid skin cleanser composition which incorporates polyvinylpyrrolidone and ethylene oxide—propylene oxide—ethylene oxide (EO/PO/EO) tri-block copolymer surfactants to improve the lathering characteristics of the cleanser.

Another object of the invention is to improve the skin after-feel of a liquid skin cleanser composition both during and after drying.

A further object is to reduce the skin irritation associated with the use of liquid skin cleanser formulations. Another object of the present invention is to improve the creaminess of lathers from liquid skin cleanser compositions.

An additional object of the invention is to provide foam stability, detergency and mildness to both soap and non-soap liquid skin cleanser formulations.

SUMMARY OF THE INVENTION

These and other objects of the invention are achieved by providing a liquid skin cleanser composition having about 0.1–25% by weight of at least one ethylene oxide—propylene oxide—ethylene oxide (EO/PO/EO) tri-block copolymer nonionic surfactant having the formula:

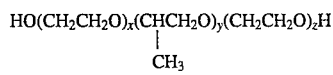

In the above formula neither x or z is 0; and the sum of x and z is within the range of about 62 to 535, the value of y is within the range of about 15 to 65. Also part of the liquid skin cleanser is about 0.1–25% by weight of polyvinylpyrrolidone having the formula:

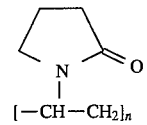

wherein the value of n ranges from about 100 to 30,000. Other ingredients may also be included, with the balance of the liquid skin cleanser being water.

DETAILED DESCRIPTION OF THE PREFERRED EMBODIMENTS

The liquid skin cleanser according to the invention will e made up of about 0.1–25% by weight of at least one ethylene oxide —propylene oxide—ethylene oxide (EO/PO/EO) tri-block copolymer nonionic surfactant having the formula:

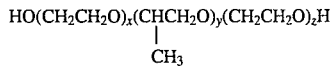

wherein neither x or z is 0; and the sum of x and z is within the range of about 62 to 535, wherein further, x=31 to 268; z=31 to 266. The value of y is within the range of about 15 to 65. The EO/PO/EO triblock copolymers of the present invention are prepared according to methods known to those skilled in the art and according to U.S. Pat. No. 2,674,619 incorporated by reference herein.

Further comprising the skin cleanser formulation will be about 0.1–25% by weight of polyvinylpyrrolidone having the formula:

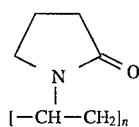

wherein the value of n ranges from about 100 to 30,000. Unless otherwise specified, all percentages expressed herein are set forth in terms of weight based upon the total weight of the composition.

In a preferred embodiment of the invention, there will be about 0.1–10% by weight of nonionic surfactant having the above formula in the liquid skin cleanser composition. Even more preferably, the nonionic surfactant will make up about 0.1–5% by weight of the formulation.

The value of the sum of x and z in the nonionic surfactant component should be within the range of about 70 to 480, wherein further x=35 to 240; z=35 to 240. It is preferred that the sum of x and z be within the range of about 82 to 480, wherein further, x=41 to 240 and z=41 to 240.

The value of y in the formula for the nonionic surfactant is preferred to be within the range of about 15 to 51, more preferably about 40 to 51.

In a more preferred embodiment of the invention, the sum of x and z will be about 200, x=100 and z=100, and the value of y will be about 65.

Further, in a most preferred embodiment of the invention, the sum of x and z will be about 266; x=133 and z=133, and the value of y will be about 50.

Two EO/PO/EO tri-block copolymer nonionic surfactants for use with the present invention include PLURONIC® F 108 and F 127, are marketed by BASF Corporation, Mt. Olive, N.J. under the trademark PLURONIC®.

Polyvinytpyrrolidone is also added to the liquid skin cleanser formulation to improve the foam character, afterfeel and rinsability. Usable species will be selected from the monomer structure:

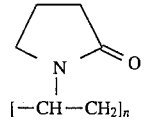

with n having a value of 100 to 30,000 as an average.

The polyvinylpyrrolidone will be present in an amount of about 0.1–25% by weight of the composition. It is more desirable that the composition contain about 0.1–10% by weight of polyvinylpyrrolidone. Even more preferably, there will be about 0.1–5% by weight of polyvinylpyrrolidone present in the liquid skin cleanser formulation of the invention.

It is also highly desirable that the ratio of polyvinylpyrrolidone and nonionic surfactant present in the liquid skin formulation be about 3:1 to 1:3. Especially desirable is the range of about 1:1.

The value of n in the formula above for the polyvinylpyrrolidone will be within the range of about 100 to 30,000. Even more preferably, this value will be within the range of about 200 to 30,000. When n is within the range of about 300 to 30,000, the polyvinylpyrrolidone will be especially preferred as a component of the liquid skin cleanser formulation.

An especially desirable embodiment of the invention will include polyvinylpyrrolidone wherein n has a value of about 380.

The liquid skin cleanser composition according to the various embodiments of the invention may also contain one or more additional components. These will include one or more anionic surfactants selected from the group consisting of soaps, detergents, sulfates, sulfonates, sulfosuccinates, isethionates and betaines, as well as other anionic surfactants known to those skilled in the art. These may be added in amount of from about 1–40% by weight of the composition based on weight, more preferably about 10–25% by weight and even more preferably about 12–20% by weight of the composition. In an especially desirable embodiment, the anionic surfactant(s) will comprise about 15% by weight of the liquid skin cleanser composition. Two suitable examples of anionic surfactants will include sodium lauryl ether (3) sulfate and ammonium lauryl sulfosuccinate.

Also to be included as part of the invention may be one or more foam stabilizers. Thee may comprise about 0.1 to 10% by weight of the liquid skin cleanser composition, more preferably about 2–7% by weight, and even more desirably about 3–5% by weight. These foam stabilizers may include, for example, lauric acid diethanolamide.

The composition of the invention may also contain one or more additional ingredients selected from the group of thickeners, fragrances, colors and pearlizing agents, etc. An example of a suitable thickener would be sodium chloride. Other thickeners may also be added in amounts of from about 0.1–5% by weight of the skin care composition.

Water will make up the remainder of the composition.

The various components of the liquid skin cleanser composition are mixed together according to methods known in the art to obtain the final composition.

EXAMPLE

The following example will illustrate a preferred embodiment of the invention, but should not be construed as limiting the scope thereof.

A generic skin cleanser composition was developed and is listed below:

| | |
|---|---|
| Sodium Lauryl Ether (3) Sulfate (28% active) | 28.0% w/w |
| Ammonium Lauryl sulfosuccinate (40% active) | 12.5 |
| Lauric Diethanolamide | 3.0 |
| Sodium Chloride | 4.5 |
| Water | 52.0 |

To this formulation were added varying concentrations of ethylene oxide—propylene oxide—ethylene oxide (EO/PO/EO) tri-block copolymer surfactants and/or polyvinylpyrrolidone (PVP), at the concurrent expense of the level of water listed above. The EO/PO/EO tri-block copolymer utilized corresponded to the formula heretofore set forth with the sum of x and z being about 266, x=133; z=133, and the value of y being about 50 (PLURONIC® F 108). The PVP utilized had a molecular weight of about 40,000, corresponding to an n value of 380.

In-house panel tests, using 12 laboratory personnel as consumer-oriented evaluators, were conducted. The panelists were uniformly instructed to wash their hands with IVORY® bar soap, dry their hands, and then wash in a specified manner with each version (Formulas 1–9) of the liquid hand soap. The protocol was as follows: Each panelist applied one pump-full of the liquid skin cleanser into the palm of one hand. The palm of the other hand was then pre-wet. Next, both palms were rubbed together 15 times in a back and forth motion. The panelists then rated each product on a scale of 0–5 (5: highest rating; 0: lowest rating) for the following parameters: speed of lather formation and creaminess of the lather. Next, the panelists dried their hands and rated each product on the following: stickiness of the hands while drying, slip imparted by the formula on the hands and the moisturized feel on the hands caused by the product. Note that it is desirable to attain the LOWEST possible score for stickiness. finally, the panelists thoroughly washed both hands for ten seconds again with IVORY® bar soap, rinsed and dried before preceding to the next liquid soap. The average scores are set forth below. Formula 4) represents a preferred embodiment of the invention, while the other formulas are comparative examples:

| FORMULA | SPEED | CREAMY | STICKY | SLIP | MOIST |
|---|---|---|---|---|---|
| 1 Formula I | 2.98 | 2.80 | 2.86 | 2.11 | 2.00 |
| 2 5% Surfactant | 3.18 | 2.90 | 1.78 | 1.95 | 2.95 |
| 3 54; PVP | 2.73 | 3.33 | 2.73 | 2.38 | 2.80 |
| 4 2%:2% surf: PVP | 3.00 | 2.90 | 1.58 | 2.73 | 3.00 |
| 5 DIAL® Anti-bacterial | 2.45 | 2.70 | 2.30 | 1.98 | 2.45 |
| 6 DIAL® Moisturizers w/Vit. E | 2.88 | 3.48 | 2.13 | 2.35 | 2.75 |
| 7 SOFTSOAP® Sensitive Skin | 2.36 | 2.34 | 1.56 | 2.47 | 2.39 |
| 8 IVORY® | 2.73 | 2.70 | 2.86 | 2.00 | 2.39 |
| 9 LEVER® 2000 | 3.05 | 3.20 | 1.88 | 2.75 | 2.98 |

It should be noted that LEVER 2000 contains a fragrance that is credited for much of the product's popularity. Panelists' remarks indicated that the fragrance had a real impact on evaluation results. Formulas 1 through 4 were unfragranced.

These results indicate that desirable tactile properties may be improved without the use of exotic and expensive additives. Moreover, the fact that the surfactants and polymers as part of the invention are nonionic in nature imply that such prototype systems may incorporate other additives which might not be compatible with soap-based systems.

While the invention has been described in each of its various embodiments, it is expected that certain modifications thereto may be made by those skilled in the art without departing from the true spirit and scope of the invention as set forth in the specification and the accompanying claims.

What is claimed is:

1. A liquid skin cleanser composition, comprising:
   a) about 0.1–25% by weight of at least one ethylene oxide—propylene oxide—ethylene oxide (EO/PO/EO) tri-block copolymer nonionic surfactant having the formula:

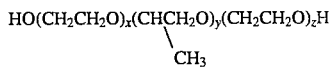

wherein the sum of x and z is within the range of about 62 to 535, and neither x or z can be 0; the value of y is within the range of about 15 to 65;

b) about 0.1–25% by weight of polyvinylpyrrolidone having the formula:

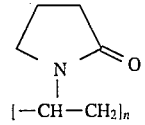

wherein the value of n ranges from about 100 to 30,000;

c) about 5–40% by weight of one or more anionic surfactants; and
   d) water.

2. A composition according to claim 1, wherein x is within the range of about 31 to 266; z is within the range of about 31 to 266.

3. A composition according to claim 1, wherein x is within the range of about 35 to 240; z is within the range of about 35 to 240.

4. A composition according to claim 1, wherein x is within the range of about 41 to 240; z is within the range of about 41 to 240.

5. A composition according to claim 1, wherein x=100 and z=100.

6. A composition according to claim 1, wherein x=133 and z=133.

7. A composition according to claim 1, wherein y=40–65.
8. A composition according to claim 2, wherein y=40–65.
9. A composition according to claim 3, wherein y=40–65.
10. A composition according to claim 4, wherein y=40–65.
11. A composition according to claim 5, wherein y=40–65.
12. A composition according to claim 6, wherein y=40–65.
13. A composition according to claim 11, wherein y=65.
14. A composition according to claim 12, wherein y=50.
15. A composition according to claim 12, wherein n=380.
16. The composition as claimed in claim 1, comprising about 0.1–10% by weight of said EO/PO/EO nonionic surfactant and about 0.1–10% by weight of said polyvinylpyrrolidone.
17. The composition as claimed in claim 13, comprising about 0.1–10% by weight of said EO/PO/EO nonionic surfactant and about 0.1–10% by weight of said polyvinylpyrrolidone.
18. The composition as claimed in claim 14, comprising about 0.1–10% by weight of said EO/PO/EO nonionic surfactant and about 0.1–10% by weight of said polyvinylpyrrolidone.

* * * * *